(12) United States Patent
Ouellette

(10) Patent No.: US 9,980,792 B2
(45) Date of Patent: May 29, 2018

(54) HYBRID TEMPORARY ANCHORAGE DEVICE IMPLANT SYSTEM AND ASSOCIATED METHODS

(71) Applicant: Paul Ouellette, Cocoa, FL (US)

(72) Inventor: Paul Ouellette, Cocoa, FL (US)

( * ) Notice: Subject to any disclaimer, the term of this patent is extended or adjusted under 35 U.S.C. 154(b) by 0 days. days.

(21) Appl. No.: 15/494,698

(22) Filed: Apr. 24, 2017

(65) Prior Publication Data

US 2017/0245964 A1    Aug. 31, 2017

Related U.S. Application Data

(63) Continuation of application No. 14/297,894, filed on Jun. 6, 2014, now Pat. No. 9,629,696.

(60) Provisional application No. 61/832,261, filed on Jun. 7, 2013.

(51) Int. Cl.
    *A61C 8/00* (2006.01)
    *A61C 7/00* (2006.01)
    *A61C 13/107* (2006.01)

(52) U.S. Cl.
    CPC ............ *A61C 8/00* (2013.01); *A61C 7/00* (2013.01); *A61C 8/006* (2013.01); *A61C 8/0012* (2013.01); *A61C 8/0024* (2013.01); *A61C 8/0068* (2013.01); *A61C 8/0069* (2013.01); *A61C 8/0078* (2013.01); *A61C 8/0096* (2013.01); *A61C 13/0001* (2013.01); *A61C 2008/0084* (2013.01); *A61C 2201/005* (2013.01)

(58) Field of Classification Search
    CPC ....... A61C 8/00; A61C 8/0012; A61C 8/0024; A61C 8/006; A61C 8/0068; A61C 8/0069; A61C 8/0078; A61C 8/0096

USPC .................................................. 433/172–176
See application file for complete search history.

(56) References Cited

U.S. PATENT DOCUMENTS

| | | | |
|---|---|---|---|
| 5,302,126 A * | 4/1994 | Wimmer | A61C 8/0022 433/173 |
| 5,622,500 A * | 4/1997 | Niznick | A61C 8/0048 206/63.5 |
| 5,873,720 A | 2/1999 | Jorneus et al. | |
| 2004/0209226 A1* | 10/2004 | Rogers | A61C 8/0001 433/173 |
| 2007/0111163 A1 | 5/2007 | Powell et al. | |
| 2007/0202462 A1 | 8/2007 | Schwarz et al. | |
| 2007/0298377 A1* | 12/2007 | Kenealy | A61C 8/0012 433/173 |

(Continued)

OTHER PUBLICATIONS

Wilmes et al., "Mini-Implant-Supported Temporary Pontics", JCO, Inc., Jul. 2014, 8 pages.

(Continued)

*Primary Examiner* — Yogesh Patel
(74) *Attorney, Agent, or Firm* — Maxine L. Barasch; Keohane & D'Alessandro, PLLC

(57) ABSTRACT

A hybrid temporary anchorage device implant system and method of use is disclosed. A temporary anchorage device (TAD) implant includes an external hex head, a cupped inner portion, a threaded core, a platform, and an implant portion. A first abutment is installed on the implant portion. The first abutment may include a graduated portion, a screw-retained healing collar, and a threaded portion. A second abutment may be installed over the first abutment. The second abutment may include a graduated head, a bulbous base, and an inner canal.

16 Claims, 7 Drawing Sheets

(56) References Cited

U.S. PATENT DOCUMENTS

2009/0104585 A1   4/2009  Diangelo et al.
2010/0143869 A1*  6/2010  Padros Fradera ...... A61C 8/005
                                                      433/174

OTHER PUBLICATIONS

Paquette, David E., "Miniscrew-Supported Transitional Tooth Replacement: An Esthetic Alternative", JCO, Inc., vol. XLIV, No. 5, May 2010, pp. 321-325.
Singh et al., "Miniscrew Supported Interim Tooth Replacement: A Temporary Alternative", The Journal of Indian Orthodontic Society, Apr.-Jun. 2012, 46(2), pp. 113-115.
Kalia, Ajit, Mini Screw Orthodontic Implant as Temporary Crown Restoration to Replace Unilateral Missing Lateral Incisor post-Orthodontic Treatment, Journal of Oral Implantology, vol. XLI, No. 3, 2015, pp. 306-309.
Schulte, Michael, Temporary Anchorage Device (TAD) Supported Pontics Prevent Bone Resorption in Young Growing Patients with Missing Maxillary Lateral Incisors, https://cats.uthscsa.edu/published_cats_friendly_php? d=2964, Dec. 10, 2015, 2 pgs.
Cope et al., "Temporary replacement of missing maxillary lateral incisors with orthodontic miniscrew implants in growing patients: rationale, clinical technique, and long-term results", JO Sep. 2014, 13 pgs.
Waugh, Robert, "CBCT and Barium Markers When Placing Temporary Implants: How can I use CBCT and barium markers when placing temporary implants?" The Dentists' Voice, 2012, 2 pgs.
Andrade et al., "Treatment for agenesis of maxillary lateral incisors: a systematic review", Orthodontics & Craniofacial Research, 2013, 9 pages.
Graham, John W., "Temporary Replacement of Maxillary Lateral Incisors with Miniscrews and Bonded Pontics", Journal of Clinical Orthodontics, vol. 41, Issue 6, 2007, pp. 321-325.
Kavedia et al., "Agenesis of maxillary lateral incisors: a global overview", Orthodontics: the art and practice of dentofacial enhancement, UMKC Dental Library Periodical, vol. 12, No. 4, 2011, pp. 296-317.
Uribe et al., "Cone-beam computed tomography evaluation of alveolar ridge width and height changes after orthodontic space opening in patients with congenitally missing maxillary lateral incisors", American Journal of Orthodontics and Dentofacial Orthopedics, vol. 144, Issue 6, Dec. 2013, pp. 848-859.
Kokich et al., "Congenitally missing maxillary lateral incisors: Restorative replacement", American Journal of Orthodontics and Dentofacial Orthopedics, Apr. 2011, vol. 139, Issue 4, pp. 435-445.
Pini et al., "Congenitally Missing Maxillary Lateral Incisors: update on the Functional and Estehtic Parameters of Patients Treated with Implants or Space Closure and Teeth Recontouring", The Open Dentistry Journal, 2014, 10 pages.
Kokich, Vince, Jr., "Early Management of Congenitally Missing Teeth", Seminars in Orthodontics, 11, pp. 146-151.
Flanagan, Dennis, "Fixed Partial Dentures and Crowns Supported by Very Small Diameter Dental Implants in Compromised Sites", Implant Dentistry, vol. 17, No. 2, pp. 182-191.
Kinzer et al., "Managing Congenitally Missing Lateral Incisors, Part II: Tooth-Suported Restorations", Journal of Esthetic and Restorative Dentistry, vol. 17, 2005, pp. 76-84.
Kinzer et al., "Managing Congenitally Missing Lateral Incisors, Part IiI: Single-Tooth Implants", Journal of Esthetic and Restorative Dentistry, vol. 17, 2005, pp. 202-210.
Gurgel et al., "Mini-Implants as Provisional Anchorage for the Replacement of Missing Anterior Teeth: A Clinical Report", The Journal of Prosthetic Dentistry, 112, 2014, pp. 706-709.
Giannetti, "Mini-implants in growing patients: a case report", Pediatric Dentristy, vol. 32, Issue 3, 2010, pp. 239-246.
Mazor et al., "Mini-Implants to Reconstruct Missing Teeth in Severe Ridge Deficiency and Small Interdental Space: A 5-Year Case Series", Implant Dentistry, vol. 13, No. 4, 2004, pp. 336-341.
Bhalla et al., "Miniscrew design and bone response: Defining a correlation", Scientific Innovation, vol. 14, 2013 13 pages.
Ciarlantini et al., "Miniscrew-retained pontics in growing patients: a biological", Journal of Clinical Orthodontics, vol. 46, Issue 10, Oct. 2012, pp. 638-640.
Gleiznys et al., "New approach towards mini dental implants and small-diameter implants: an option for long-term prostheses", Stomatologija Baltic Dental and Maxillofacial Journal, vol. 14, No. 2, 2012, pp. 39-45.
Keller, G. William, "Temporarily Replacing Congenitally Missing Maxillary Lateral Incisors in Teenagers Using Transitional Implants", Dental Tribune, Jul.-Sep. 2003, No. 2, vol. 1, 2 pages.
Patel, U.S. Appl. No. 14/297,894, Notice of Allowance & Fees Due, dated Dec. 22, 2016, 10 pgs.

* cited by examiner

HYBRID TEMPORARY ANCHORAGE DEVICE IMPLANT SYSTEM AND ASSOCIATED METHODS

CROSS-REFERENCE TO RELATED APPLICATION

The present patent document claims the benefit of the filing date of U.S. patent application Ser. No. 14/297,894, filed Jun. 6, 2014, the disclosure of which is incorporated herein by reference.

FIELD OF THE INVENTION

The present invention relates to the field of orthodontic implants and, more specifically, to the field of hybrid temporary anchorage device implants for both short term use and long term use.

BACKGROUND OF THE INVENTION

It is well known that temporary anchorage devices (TADs) have been used for years in orthodontic therapy to attempt to overcome the limitations of conventional orthodontic anchorage devices. A provisional implant or TAD is a device that is temporarily fixed to bone for the purpose of enhancing orthodontic anchorage either by supporting a tooth or group of teeth acting as anchorage during movement of another tooth or group of teeth, or by obviating the need to use a tooth or a group of teeth as anchorage altogether. A TAD is typically removed after use. Anchorage by means of TADs allows independence in relation to patient compliance. TADs can be located transosteally, subperiosteally, or endosteally; and they can be fixed to bone either mechanically (cortically stabilized) or biochemically (osseointegrated). TADs are typically designed to be immediately loaded (the application of pressure from the TAD to a tooth or group of teeth by use of nickel titanium springs, elastic power chain modules, or other means of exerting force.) TADs are designed to be easily inserted and easily removed at will. TADs all mechanically integrate, but do not integrate to the point that they cannot be easily removed.

By contrast, the majority of regular root form/endosseous implants are designed to super integrate or biologically integrate. By osseointegrating in the surrounding bone, root form implants can endure/last almost permanently. Endosseous implants are designed for longevity (long term integration with the bone) not as a temporary implant that can be easily removed. Root form implants are more expensive than TADs. As a result of the expense of root form implants, oftentimes patients wait years between a tooth extraction and the implantation of a root form implant while they save up their money for the procedure. Bone in the mouth that is not used or stimulated will resorb up to 50 to 60% in 5 years as a result of disuse atrophy.

There exists a need to provide a system of temporary implants, surgical instruments and abutments that provides an affordable hybrid TAD implant that mechanically integrates with cortical bone to permit long term use, but that is also easily removed, making it suitable for use in short term applications.

SUMMARY OF THE INVENTION

Such needs are addressed in the present invention. The hybrid temporary anchorage device implant system of an embodiment of the present invention may advantageously provide a dental implant that will mechanically integrate or "fibro-osseo-integrate", providing suitable anchorage for a temporary crown or other long term use, but not biologically or "permanently" integrate, permitting easy removal of the dental implant. The hybrid temporary anchorage device implant system of an embodiment of the present invention may act as a "placeholder" implant that can be easily backed out of (i.e. removed from) a patient's jawbone tissue to be replaced by a full-size implant as required. The hybrid temporary anchorage device implant system of an embodiment of the present invention may preserve cortical bone and crestal bone, thereby eliminating the need for expensive and painful future bone grafting procedures. The hybrid temporary anchorage device implant system of an embodiment of the present invention may assist with emergence profile development, tissue sculpting and socket forming. The hybrid temporary anchorage device implant system according to an embodiment of the present invention may assist with orthodontic tooth movement. The hybrid temporary anchorage device implant system of another embodiment of the present invention may be used to attach an abutment and temporary crown for several months to several years. A method of using a hybrid temporary anchorage device implant system according to an embodiment of the present invention may also be provided.

These and other objects, features and advantages according to an embodiment of the present invention are provided by a hybrid temporary anchorage device implant system that may comprise at least one TAD implant, and at least one abutment. In some embodiments, two abutments may be provided—a first (or "inner") abutment and a second (or "outer") abutment. The TAD implant may include an external hex head, a cupped inner portion, a threaded core, a platform, and an implant portion. In some embodiments, the implant portion may have self-tapping threads disposed thereon. The first abutment may include a graduated portion, a threaded portion, and a junction therein between. The second abutment may include a graduated head, a bulbous base, and an inner canal.

The method of using a hybrid temporary anchorage device implant system may comprise attaching a first abutment to a TAD implant, inserting an implant portion of the TAD implant (with the titanium abutment attached) into the bone of a patient, and fitting a second abutment over an exterior of the first abutment. More specifically, in some embodiments, the method may comprise fitting a titanium abutment into a threaded core of a TAD implant, administering an appropriate anesthetic to a patient, removing gingival tissue from the cortical plate, preparing an osteotomy by penetrating the cortical bone, expanding the cortical plate, the crestal bone at the alveolar crest and the cancellous bone at the radicular portion of the osteotomy; inserting the TAD implant having the first abutment fitted thereon to its final depth in the bone, and reducing the size of the first abutment if necessary. In some embodiments, a second abutment is fitted over the first abutment following such installation of the TAD implant into the bone, and the length of the second abutment is reduced as necessary.

BRIEF DESCRIPTION OF THE DRAWINGS

The accompanying drawings, which are incorporated in and constitute a part of this specification, illustrate several embodiments of the present teachings and together with the description, serve to explain the principles of the present teachings. Certain elements in some of the figures may be omitted, or illustrated not-to-scale, for illustrative clarity.

The cross-sectional views may be in the form of "slices", or "near-sighted" cross-sectional views, omitting certain background lines which would otherwise be visible in a "true" cross-sectional view, for illustrative clarity. Furthermore, for clarity, some reference numbers may be omitted in certain drawings. All measurements noted herein are approximate regardless of whether such is specifically noted.

DETAILED DESCRIPTION OF THE PREFERRED EMBODIMENT

Figure 1A:
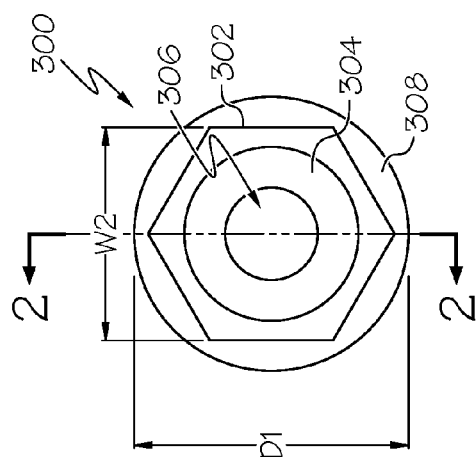
FIG. 1A is a side view of a TAD implant according to an embodiment of the present invention.

The present invention will now be described fully hereinafter with reference to the accompanying drawings, in which preferred embodiments of the invention are shown. Like numbers refer to like elements throughout. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art will realize that the following embodiments of the present invention are only illustrative and are not intended to be limiting in any way. Other embodiments of the present invention will readily suggest themselves to such skilled persons having the benefit of this disclosure. Illustrative embodiments will now be described more fully herein with reference to the accompanying drawings, in which embodiments are shown. This disclosure may, however, be embodied in many different forms and should not be construed as limited to the embodiments set forth herein. Rather, these embodiments are provided so that this disclosure will be thorough and complete and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof. The term "include" as used herein shall have the same interpretation as the term "comprise".

Reference throughout this specification to "one embodiment," "an embodiment," "embodiments," "exemplary embodiments," "some embodiments," or similar language means that a particular feature, structure, or characteristic described in connection with the embodiment is included in at least one embodiment of the present invention. Thus, appearances of the phrases "in one embodiment," "in an embodiment," "in embodiments", "in some embodiments", and similar language throughout this specification may, but do not necessarily, all refer to the same embodiment. It will be understood that one skilled in the art may cross embodiments by "mixing and matching" one or more features of one embodiment with one or more features of another embodiment.

The terms "overlying" or "atop", "positioned on, "positioned atop", or "disposed on", "underlying", "beneath" or "below" mean that a first element, such as a first structure (e.g., a first layer) is present on a second element, such as a second structure (e.g. a second layer) wherein intervening elements, such as an interface structure (e.g. interface layer) may be present between the first element and the second element.

A hybrid temporary anchorage device implant system according to an embodiment of the present invention can advantageously provide a long-term use dental implant that does not fully or completely osseointegrate. More specifically, the hybrid temporary anchorage device implant system according to the present invention advantageously provides a dental implant that engages cortical bone, sculpts soft tissues, such as gingiva (i.e. gum tissue), and stabilizes crestal bone (preventing disuse atrophy), but is still capable of being easily removed at will. The inventive TAD implant system may be used in pediatric, adolescent, and adult patients as "placeholder" or provisional implant that will prevent or slow the onset of disuse atrophy and crestal bone resorption. For example, a pediatric cleft palate patient that receives a bone graft to repair the cleft at age 10 years or younger will, more likely than not, naturally loose the repair graft over time. The novel TAD implant system is designed to prevent this naturally occurring unfavorable phenomenon. This is accomplished by the unique design of the TAD implant and abutment according to an embodiment of the present invention that can advantageously provide either a short term temporary anchorage device, like a traditional TAD, or a longer term dental implant. Installing the TAD implant system of the present invention in cleft palate patients will help retain reparative bone grafts, create biological stimulus of the grafted bone, and provide improvement of esthetics for this patient group.

Another application for the TAD implant system of the present invention is in younger patients that have conditions such as ectodermal dysplasia (ED) and hypodontia (congenitally missing less than 6 teeth). One of the symptoms of ED patients is Oligodontia or absence of 6 or more teeth. Congenitally missing one or more maxillary lateral incisors (Hypodontia) young patients may have to wait until after 25-30 years of age before conventional dental implants can be predictably placed without complications. Growth changes naturally occur in the anterior maxillary area of the jaws causing conventional implants to become, in time, esthetically compromised. Implants placed too early may lag behind the rest of the dentition (teeth) as an implant will not move, adapt or adjust with expected maxillary bone remodeling. All patients will experience (downward and forward projection of the maxilla and the natural teeth contained within the alveolar bone). The early placed dental implant and crown may appear shorter than adjacent teeth as innate growth changes of the anterior maxillary teeth continues. The dental implant crown becomes shorter or will be in a position that is termed "infra-occlusion". The TAD implant system is designed to be used in the described situations as the TAD implant can be removed anytime, extended in length at the platform level and/or replaced with another TAD implant or full sized implant, if any of the complications described occurs.

The TAD implant serves as both a TAD (a series of attachments are contemplated to use the TAD implant as an orthodontic anchor that can be immediately loaded), and as an implant designed to be used to attach an abutment and temporary crown for several months to several years. This is made possible because the TAD implant is designed for either short term use or longer term use due to an increased crestal bone surface area, i.e. implant portion, and the presence of a platform switching feature. The novel TAD implant is wider in dimension in the area where it is configured to engage the cortical plate after installation into the bone. The novel TAD implant mimics a conventional dental implant and platform to support an abutment and usual emergence profile for a provisional crown or permanent crown. If a permanent crown is installed on the TAD implant, the TAD implant and crown could be removed at will at a future time. A crown installable over the TAD implant provides esthetic improvement and psychological benefit for the patient. When the patient fully matures the TAD implant may be removed and replaced with conventional implants and permanent restorations (crowns).

Figure 1B:
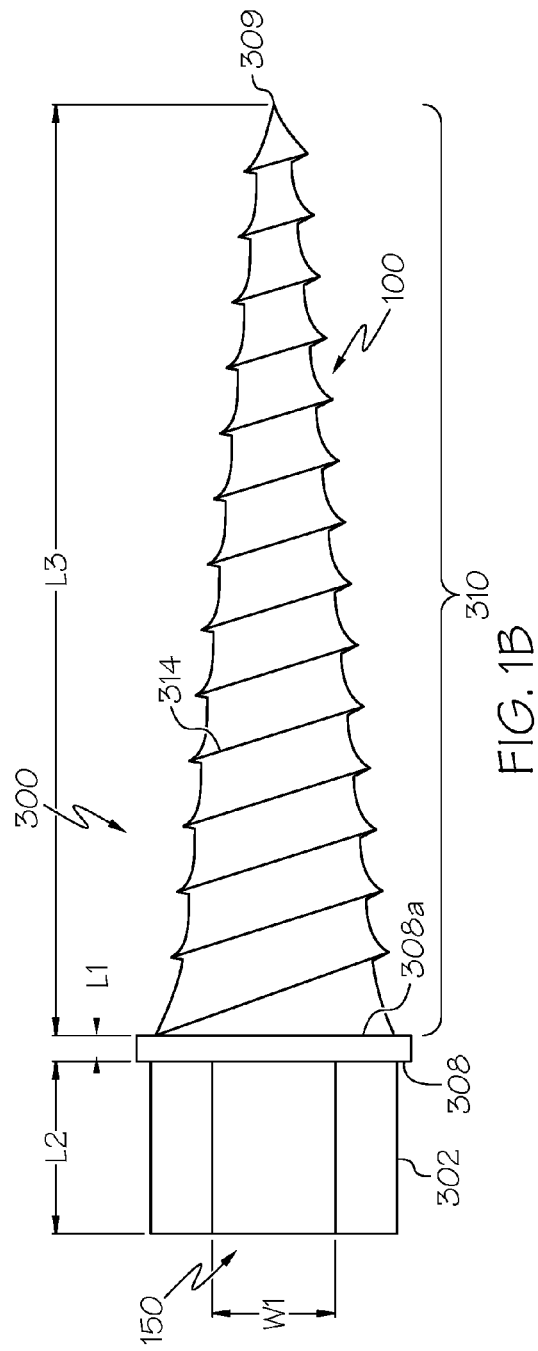
FIG. 1B is a top-down view of the TAD implant from end 150 illustrated in FIG. 1A.
Figure 2:
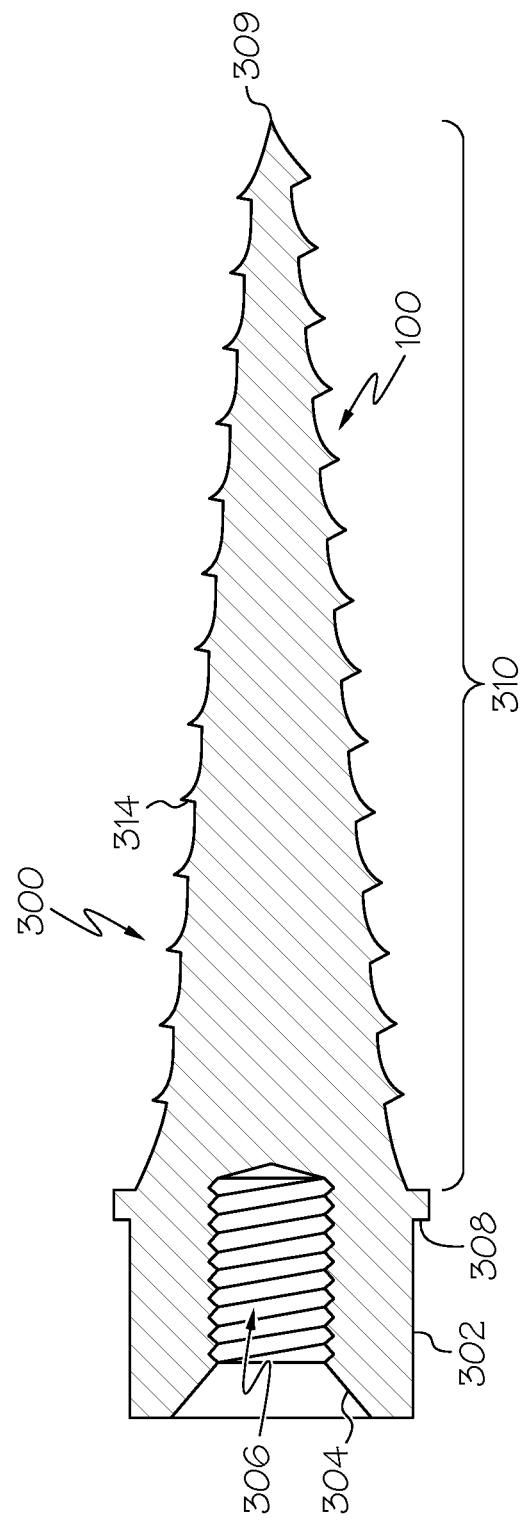
FIG. 2 is a partial cross sectional view of the TAD implant illustrated in FIG. 1 taken through line 2-2.

Referring to FIGS. 1-2, general details of the hybrid temporary anchorage device implant 300 according to an embodiment of the present invention are now described. The TAD implant 300 may include a hex head 302, a cupped inner portion 304, a threaded core 306, a platform 308, and an implant portion 310. In some embodiments, the implant portion 310 may have self-tapping threads 314 disposed thereon. The TAD implant 300 (and, therefore, the components thereof) may be manufactured using 6AL-4V Eli Titanium, Medical Grade 23. In some embodiments, the TAD implant 300 may be made from stainless steel. The implant portion is untreated, that is, not treated with anything following machining (i.e. production from the aforementioned titanium material). As a result, the implant portion has a surface less likely to completely osseointegrate like, for example, an implant that has had its surface sandblasted, plasma-sprayed and/or hydroxylapatite-coated. The inability to thoroughly osseointegrate enables removal of the TAD implant at a future time following installation into a patient's bone. Individual portions of the hybrid temporary anchorage device implant system according to an embodiment of the present invention will now be discussed in greater detail.

Figure 3A:
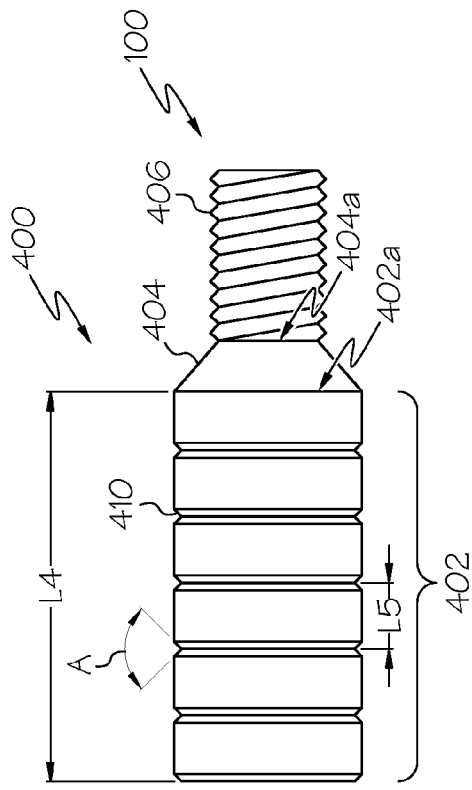
FIG. 3A is a side view of an inner/first abutment according to an embodiment of the present invention.

In embodiments, the TAD implant 300 may include a head 302 having a substantially hexagonal shape ("hex head") disposed on one side of a platform 308 formed on one end of the implant portion 310, while the other end of the implant portion 310 comprises a tip or apical portion 309 of the TAD implant. The hex head 302 is configured to be engaged by a hand or motor tool to install, i.e. "screw" the implant portion 310 into bone of a patient. The hex head 302 has a length L2. In embodiments, L2 may be approximately 2 millimeters (mm). This size was found by the inventor herein to be more resistant to fracture when applying pressure during insertion or removal of the TAD implant. The larger than typical hex head adds strength and makes the TAD implant easier to locate in the gum tissue to remove. The larger size hex length also helps the implant surgeon positively engage the TAD implant with the implant driver/removal tool to back the fixture out of the bone. This is an improvement over conventional 1 mm implant hex heads. Each side of the hex head has a width W1. In embodiments, W1 may be 2.5 mm. The width between each wall of the hex head is W2. In embodiments, W2 may be 3.4 mm. A cupped or beveled inner portion 304 may be provided within, and descending into, the hex head 302. An internal threaded core 306 may depend vertically from an inner depth of the cupped inner portion 304. The threaded core 306 is configured to accept a threaded portion 406 of an abutment 400 (FIGS. 3A-4).

The platform 308 is a prosthetic platform for support of a provisional crown. The system of embodiments of the present invention include a platform switch, which indicates that platform 308 holds an abutment (400) of a narrower diameter than the diameter of the platform 308 itself. In embodiments, the graduated portion 402 may have a diameter (D2), discussed herein below, of 2.5 mm. The platform 308 has a diameter D1, which in embodiments, be 3.4 mm. The platform 308 has a length L1. In embodiments, L1 may be 05. mm. The 2.5 mm wide titanium abutment has a dimension that is 0.9 mm narrower than the 3.4 mm platform diameter. The theory is that as compared to an implant platform and a congruent abutment (same diameter abutment), the smaller abutment diameter places the microgap or junction between the smaller sized abutment and the platform further away from the crestal bone. Thus there is less inflammatory action next to the crestal bone located just below the TAD implant platform. Platform switching decreases crestal bone loss and bone dieback to the $1^{st}$ or $2^{nd}$ threads of the self-tapping threads 310 of the TAD Implant.

The implant portion 310 is disposed on a side of the platform 308 opposite the hex head 302, and may descend therefrom at an inward taper angle. Self-tapping threads 314 may be formed on an exterior surface of the implant portion 310. The implant portion 310 has a length L3. In embodiments, L3 may be 3 mm. The implant portion 310 may terminate in a point.

Figure 3B:
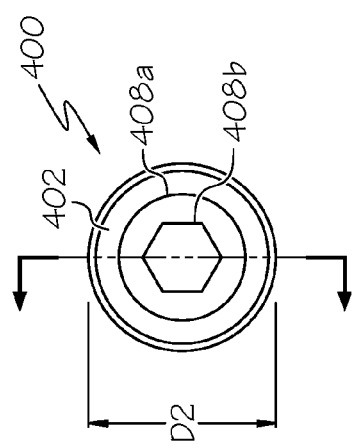
FIG. 3B is a top-down view of the end 350 abutment illustrated in FIG. 3.
Figure 4:
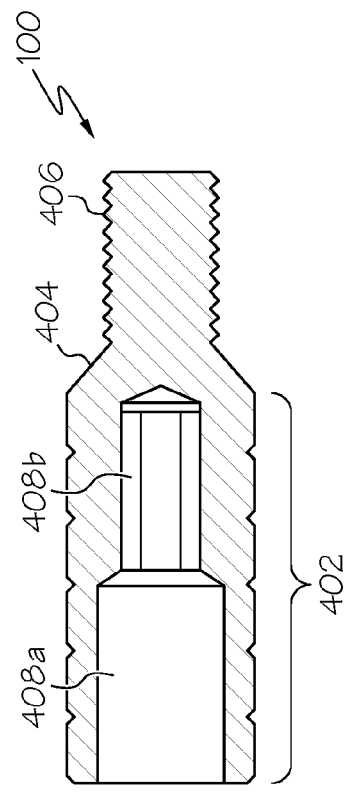
FIG. 4 is a partial cross sectional view of the outer/second abutment illustrated in FIG. 3B taken through line 4-4.

As depicted in FIGS. 3-4, the abutment 400 (also referred to as a "retaining screw") may include a graduated portion 402 and a threaded portion 406 (i.e. a screw) and an abutment driver tool indentation 408. The abutment 400 (and, therefore, the components thereof) may be manufactured using 6AL-4V Eli Titanium, Medical Grade 23. In some embodiments, the abutment 400 may be made from stainless steel. Individual portions of the hybrid temporary anchorage device implant system according to an embodiment of the present invention will now be discussed in greater detail.

As depicted in FIG. 3A, an exterior surface of the graduated portion 402 may have grooves formed thereon. The grooves 410 may provide anchorage for a temporary crown or other dental device or orthodontic device that may be affixed to the abutment 400, for example, using a cementing medium. The cement would flow into the grooves adding additional stability). The grooves 410 are indentations that span the circumference of the exterior surface of the graduated portion 402. In embodiments, the graduated portion 402 may have a maximum diameter D2 and a length L4. In embodiments, D2 may be 2.5 mm. In embodiments, L4 may be 3 mm or 6 mm. The graduated portion 402 may be reduced/trimmed to a desired length by an operator. For example, if an L4 of 5 mm is needed, then the graduated portion 402 may be trimmed from 6 mm to 5 mm. In embodiments, the grooves 410 may be distanced apart by length L5. In embodiments, L5 may be 1 mm. The walls of each of the grooves 410 descend inward to adjoin at an angle A. In embodiments, angle A may be approximately 90 degrees. Grooves 410 serve as a reference, navigation, and guide system. As grooves 410 can be viewed by radiograph (or "x-ray"), it possible to determine the depth of insertion of the TAD implant 300 in bone at the time of surgery. It also assists, therefore, in planning how much further the TAD implant 300 can be inserted or how much the TAD implant 300 should be backed out of the bone. The indexing feature makes it possible to determine the exact position of all system components. This is necessary to facilitate fabrication of a provisional crown over the abutment 400, the platform 308, and second abutment 500 (if present).

In practice, the threaded portion 406 of abutment 400 is attached, i.e. screwed, into the threaded core 306 (i.e. threaded screw receptacle) of the TAD implant 300 prior to implantation into bone of a patient. After inserting the implant portion 310 of the TAD implant 300 a distance into the bone (e.g., approximately 33% or 50% of the desired depth), a diagnostic x-ray may be taken to determine if the operator is staying clear of adjacent tooth roots or other significant anatomical structures, such as perforating any cortical plates. The grooves 410 provide a measurable scale that is helpful in determining the depth of insertion. If it is determined that the TAD implant 300 is not being inserted correctly, the direction or angle of insertion may be modified to safely insert the implant portion 310 to full depth (up to a lowest extent of the platform 308, indicated as 308a on FIG. 1).

The junction 404 may be formed on a narrowest extent of the graduated portion 402, indicated as 402a on FIG. 3A, and may descend therefrom at an inward angle. The threaded portion 406 may descend from a narrowest extent 404a of the junction 404. As illustrated in FIGS. 3B and 4, the abutment driver tool indentation 408 may be formed in an inner region of the graduated portion 402 of the abutment 400. A first extent 408b of the abutment driver tool indentation 408 may have a narrower width than a second extent 408a. The abutment driver tool indentation 408 may be shaped to accept an abutment driver tool. The indentation 408 is not limited to the shape shown herein, but may be varied to accommodate the driver tool intended for use therewith.

In some embodiments of the invention, the system may include the TAD implant 300 and the abutment 400. In other embodiments, the system may include the TAD implant 300, the abutment 400, and yet another abutment 500. Referring now to FIGS. 5A-6, there is shown a second abutment 500 of embodiments of the TAD implant system of the present invention. In embodiments, second abutment 500 may be fitted over the (first) abutment 400 and hex head 302 of TAD implant 300. Typically, second abutment 500 is used for tissue sculpting soft tissues such as gingiva (gum) tissue. In embodiments, the second abutment 500 may comprise polyetheretherketone type (i.e. PEEK-type) plastic. In embodiments, the second abutment 500 may comprise resin reinforced methyl methacrylate. In embodiments, the plastic may be white or tooth-colored to mask the metal-colored abutment 400 underneath.

Figure 5C:
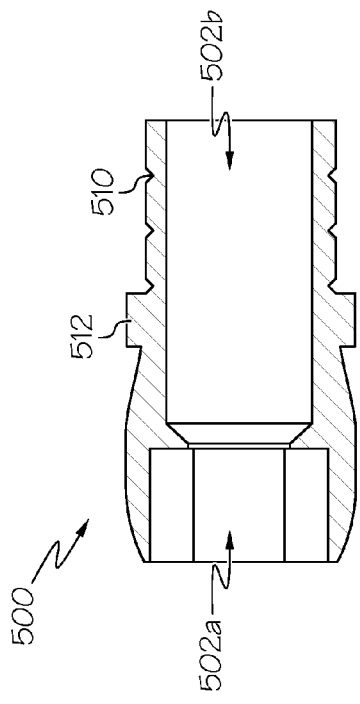
FIG. 5C is a cross-sectional view of the abutment illustrated in FIGS. 5A and 5B taken through line 5-5.
Figure 6:
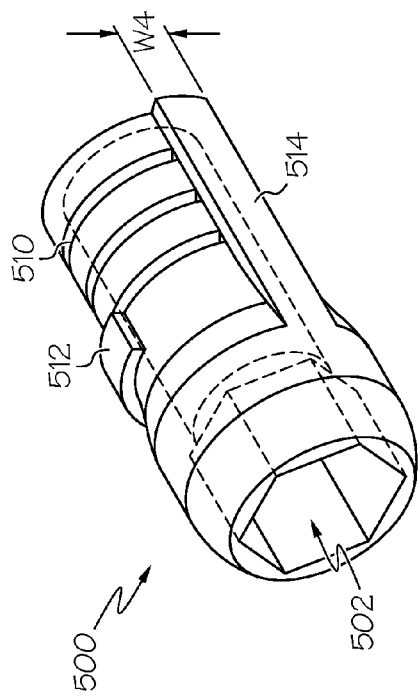
FIG. 6 is an isometric view of the outer abutment of the abutment illustrated in FIGS. 5A-5C.
Figure 5A:
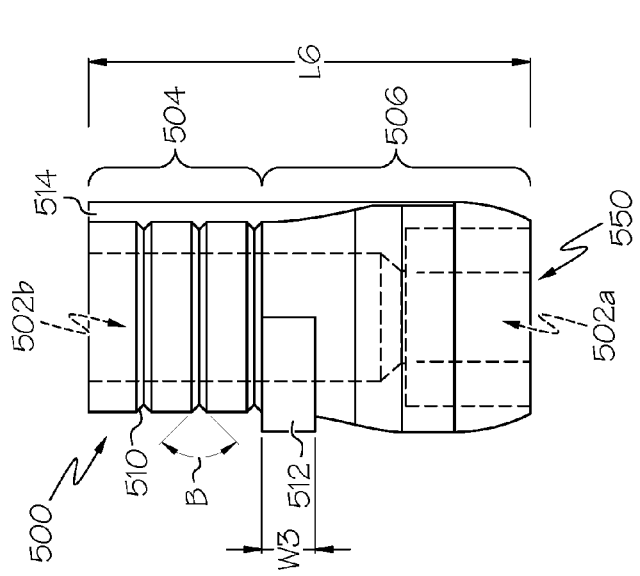
FIG. 5A is a side view of the outer abutment illustrated in FIG. 4.
Figure 5B:
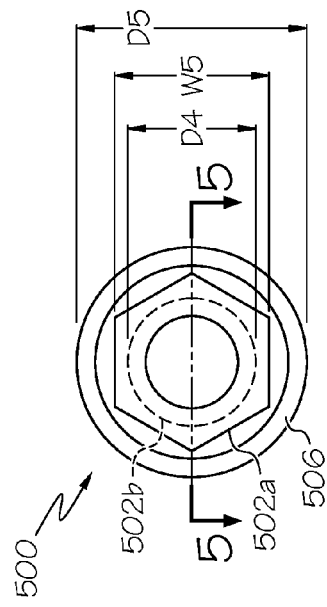
FIG. 5B is a top-down view of the abutment from side 550 illustrated in FIG. 5.

In embodiments, the second abutment 500 is elastic and "sleeve-like" in design, having an open interior canal disposed therein indicated generally as a whole as 502 on FIG. 6 and as 502a and 502b to designate its parts on FIG. 5C. The inner canal 502 is configured to frictionally engage (i.e. "hug") the exterior surface of (first) abutment 400 and the hex head 302 of the TAD implant 300, and an adhesive cement may be used to secure the abutment 500 in place. Canal 502 includes a female hex 502a for engagement of the hex head 302 and an elongated section 502b for engagement of the graduated portion 402 of the abutment 400. In embodiments, female hex 502a has a width W5 between each opposing wall. In embodiments, W5 may be approximately 3.43 mm (i.e. slightly larger than the hex head 302 to fit around the hex head 302). In embodiments, elongated portion 502b may have a diameter D4. In embodiments, D4 may be approximately 2.5 mm (to cover elongated portion 402). Second abutment 500 has a length L6. In embodiments, L6 may be approximately 6.5 mm (to cover the length of the abutment 400 and the length of hex head 302). In embodiments, the length (L6) may be adjusted (by trimming, for example) to fit the length the hex head 302 and abutment (if reduced), or for example, to avoid a portion of abutment 500 protruding upward from the installed abutment 400/TAD implant 300 in a patient's mouth from interfering with opposite dental arch teeth. If the plastic or abutments are too long, they may hit the opposing tooth. Therefore, an operator may reduce/trim off the interfering portion. Without such reduction, the abutment(s) could interfere with chewing, swallowing and talking.

Second abutment 500 has a graduated portion 504 and a bulbous base 506. In embodiments, the bulbous base has a maximum diameter selected from a first size, a second size, or a third size. In embodiments, the first size may be approximately 3.4 mm, the second size may be approximately 4.5 mm, and the third size may be approximately 5.5 mm. The plurality of diameters allows an initial installation of a plastic abutment of a first size on to a hex head 302 and graduated portion 402 to sculpt an initial emergence or tooth socket of a first diameter. In practice, a second abutment 500 having a maximum diameter of 3.4 mm is fitted onto the implant 300 situated in the bone of a patient. The second abutment is secured to the TAD implant by screwing the first abutment back into the threaded cored 306. The first diameter of the abutment 500 is substantially congruent with the platform 308 diameter to sculpt the tissue to about 3.4 mm). So in time, the tooth socket formed by tissue surrounding the base 506 of abutment 500 enlarges to a size of the diameter of the abutment 500. The first plastic abutment (500) is then removed from the abutment (400) and replaced with a second plastic abutment (500) having an exterior diameter of the second size. In time, the tooth socket will widen to the diameter of the second size (wider than the first size). The second plastic abutment (500) is then replaced with a third plastic abutment (500) having an external diameter of a third size to widen the tooth socket to the diameter of the third size (wider than the second size). This allows the enlargement of the future crown emergence up to, for example, a 5.5 mm diameter.

Like the abutment 400, the abutment 500 includes a graduated portion 504 having grooves 510 on the outer surface of the graduated portion. The grooves 510 give an operator a visual reference of scale when working in the mouth or inspecting the titanium grooves that show up on a periapical x-ray. The grooves 510 on the plastic abutment will not show up on x-ray if a radiopaque plastic is not used. If a radiopaque material is used, then the grooves will show up on x-ray. The radiopaque material may be advantageous as it enables the operator to observe a junction between a provisional crown—and the TAD implant 300 to determine whether the plastic abutment 500 is fully seated on the platform 308. Grooves 510 are distanced apart by length L7. In embodiments, L7 may be approximately 1 mm. The walls of each of the grooves 510 descend inward to adjoin at an angle B. In embodiments, angle B may be approximately 90 degrees.

In embodiments, second abutment 500 has a plurality of elevations (i.e. raised bumps) disposed on the exterior surface thereof, which function as an "indexing" feature in impressions or digital scans. In the embodiment shown herein, there are two elevations. A first elevation 512 is a "horseshoe" or "half-circle"-shaped elevation extending partially around (approximately half of the circumference of) the exterior surface of the abutment 500. A second elevation 514 is "linear", originating at the approximate widest area (in diameter) of the bulbous base 506 and extending in a substantially straight direction to the opposite end of the abutment 500. The first elevation is perpendicular to the long axis of the abutment. The second elevation is parallel to the long axis of the abutment. The first elevation 512 has a width W3. In embodiments, W3 is approximately 1 mm. The second elevation 514 has a width W4. In embodiments, W4 may be approximately 1 mm.

The elevations 512, 514 is a guide system for precisely locating the precise or exact vertical, horizontal, and angular position of the TAD implant portion 310 and hex head 302 relative to the bone of a patient. The elevations 512, 514 facilitate "pick-up" or indexing the precise position of the TAD implant and attached abutment for a dental impression and/or can be detected by digital scanning. The elevations 512, 514 become pushed into an impression, or analyzed with a computer program after scanned. This allows indexing of an exact position of the abutment 500 when it is fully engaged onto the hex head 302 and graduated portion 402. The elevations 512, 514 allow the laboratory to precisely line up the exact position of the TAD implant 300's platform 308 and at what angle or position is the hex head 302 relative to the TAD implant's external hex head 302 and the relative position of the bone below and adjacent teeth. It is important to know the exact position of the plastic abutment so a provisional crown can be fabricated that will fit exactly in the mouth as it does on a laboratory model. The elevations 512, 514 can also be detected by digital scan to accomplish the same.

Figure 7:
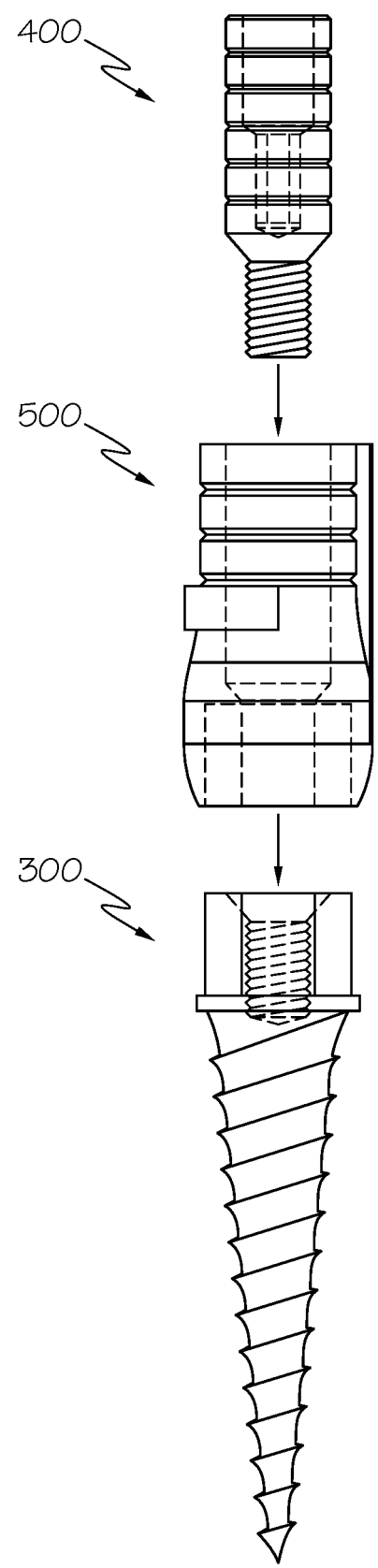
FIG. 7 is an exploded side view of a TAD implant system of the present invention.

FIG. 7 shows an exploded view of an embodiment of the implant system of the present invention. As assembled, the system may comprise the TAD implant 300, abutment 400, and second abutment 500. The second abutment 500 by female hex 502*a* fits over the hex head 302 of the TAD implant 300. The abutment 400 fits through the canal 506*b* with threaded portion screwing into the internal threaded core 306 of the TAD implant 300, and surrounding graduated portion 402 of the abutment 400. The second abutment 500 is secured in place by the abutment 400 engaging with the TAD implant 300. Additionally, adhesive cement may be used to further secure the abutment 500 to the hex head of the TAD implant 300.

Figure 8:
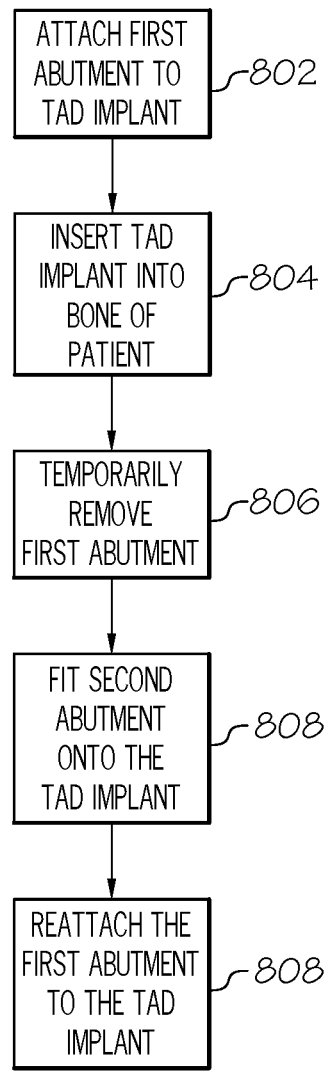
FIG. 8 is a flowchart of a method of using a hybrid temporary anchorage device implant according to an embodiment of the present invention.
Figure 9:
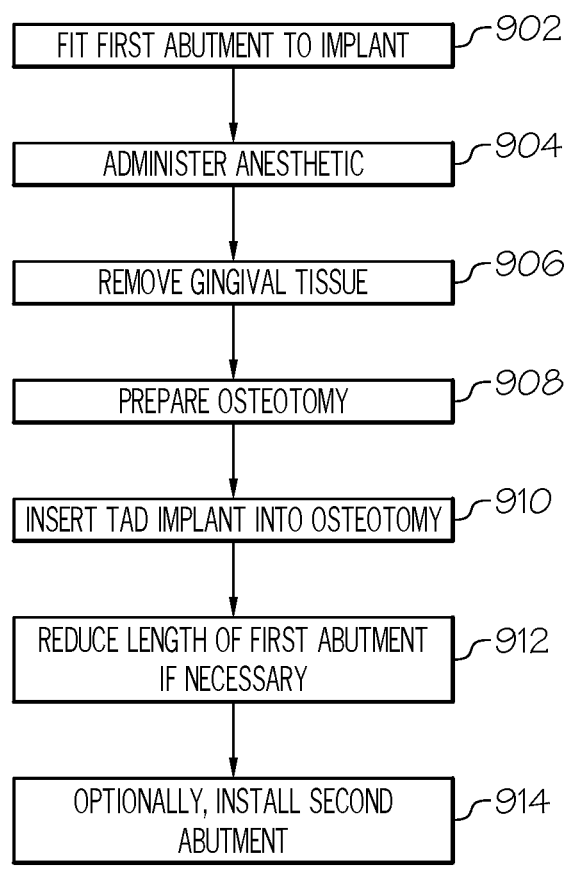
FIG. 9 is a flowchart of a method of using a hybrid temporary anchorage device implant according to an embodiment of the present invention.

FIG. 8 shows a method of using a hybrid temporary anchorage device implant according to an embodiment of the present invention may also be provided. At 802, a first abutment is attached (e.g., screwed on) to a TAD implant. At 804, the implant portion of the TAD implant is inserted into the jawbone of a patient. At 806, the first abutment is temporarily removed. At 808, a female hex (502*a*) of the second abutment is fitted over a hex head 302 of the first abutment. At 810, the first abutment is threaded through an interior elongated canal (502*b*) of the second abutment, and reattached (screwed back onto) the TAD implant. More specifically, as shown in FIG. 9, in some embodiments, the method may comprise the following. At 902, a first abutment is fitted into a threaded core of a TAD implant. At 904, an appropriate anesthetic is administered to a patient. At 906, gingival tissue is removed from the cortical plate of bone of the patient. At 908, an osteotomy is prepared by penetrating the cortical bone and expanding the cortical plate, the crestal bone at the alveolar crest, and the cancellous bone at the site of the osteotomy. At 910, the TAD implant having the abutment fitted thereon is inserted into the osteotomy. At 912, the size of the first abutment is reduced if necessary. If a second abutment is to be used, at 914, the first abutment is temporality removed, the second abutment is fitted onto the TAD implant 300, the length of the second abutment is reduced as necessary, and the first abutment is screwed back onto the TAD implant.

A set of surgical tools may be used for insertion of the assembly into a bone of a patient. Such surgical tools may include a surgical guide, a tissue punch tool, at least one reduction adapter tool, an undersized OD (4 mm outside diameter designed to accurately slide through a 4.1 mm ID surgical guide sleeve) starter drill, an undersized osteotome, a surgical hammer, a torque wrench, an extended driver socket, an implant motor, an extended driver attachment, an abutment holding tool, and an abutment driver tool. The surgical guide may be a prefabricated Cone Beam Computed Tomography created surgical guide. The surgical guide may have openings formed therein positioned in the analogous location in the surgical guide where the at least one TAD implant 300 is to be implanted in a patient's mouth. The number of openings formed in the surgical guide may correspond with the number of TAD implants 300 to be implanted. The tissue punch tool may have a diameter of 2 mm. The reduction adapter tool may have reduction collars of different sizes formed in opposite ends thereof. Each reduction collar may have an opening formed therein. The reduction collars may pass through the openings of the surgical guide. The undersized OD starter drill may pass through the opening in the reduction collar of the reduction adapter tool The undersized OD starter drill may have a diameter in the range of 1.2 mm to 1.5 mm. The undersized OD starter drill may be undersized by 1.0 mm to 0.5 mm. The undersized osteotome may pass through the opening of the surgical guide.

The undersized osteotome may be a replica of the TAD implant 300 undersized by 1.0 mm to 0.5 mm. The surgical hammer may be used to prepare an osteotomy. The torque wrench may be used in conjunction with the extended driver socket to insert the TAD implant 300 implant by hand. The extended driver socket may be sized to accommodate the TAD implant 300 with the abutment 400 installed therein. In another embodiment according to the present invention, the implant motor may be used in conjunction with the extended driver attachment to insert the TAD implant 300. The extended driver attachment may be sized to accommodate the TAD implant 300 with the abutment 400 installed therein (together as one unit). Inserting the TAD implant 300 together with the abutment 400 allows a progress radiograph to be taken to verify the correct path of insertion before the TAD implant 300 is driven into a final depth. The TAD implant 300 having the attached abutment 400 can be inserted into bone to a depth of 10 mm, to a base 308*a* of the platform 308, or the TAD implant 300 can be inserted to a depth of 12 mm if sub-crestal insertion is desired. Thereafter, in some embodiments, a second (or outer) abutment 500 may be installed over the (first, or inner) abutment 400 using a hand or motor driver. Plastic abutment is inserted by operator's fingers onto the TAD Implant platform and a 3 or 6 mm titanium retaining screw is screwed into the platform screw receptacle to tightly hold the plastic abutment into place.

The novel method may include the following using the set of surgical tools. A first abutment 400 is fitted into the threaded core of a TAD implant 300 with the abutment driver tool. The method may include administering an appropriate anesthetic to a patient, placing a surgical guide within the mouth of the patient, passing a tissue punch tool through an opening in the surgical guide, and removing gingival tissue from the cortical plate with the tissue punch tool. The patient may receive a topical anesthetic administered for a period of 5 minutes followed by local anesthetic infiltration, if required. The tissue punch tool may be used to remove 2 mm or more of gingival tissue over the cortical plate. The method may also include placing a reduction adapter tool in the opening in the surgical guide, passing an undersized OD starter drill through the reduction adapter tool, penetrating the cortical bone with the starter drill, preparing an undersized osteotomy with the starter drill, removing the reduction adapter tool from the surgical guide, passing an osteotome through the opening in the surgical guide, and expanding the cortical plate, the crestal bone at the alveolar crest and the cancellous bone at the radicular portion of an osteotomy with the osteotome. The 1.5 mm OD starter drill may be used to prepare an undersized 5 to 8 mm deep osteotomy. The osteotome may be used to further expand the cortical plate, the crestal bone at the alveolar crest and the cancellous bone at the root end of the osteotomy to a depth of 10 mm. The method may further include preparing the osteotomy with a surgical hammer by gently tapping.

In some embodiments, the surgical guide may then be removed from the patient's mouth, and TAD implant 300 having the abutment 400 fitted thereon is inserted to its final depth with a torque wrench with extended driver socket or with an implant motor with extended driver socket.

In some embodiments, rather than remove the surgical guide, the surgical guide may be left in place. An extended driver socket may be used with the surgical guide. The OD is 4 mm and the throat of the driver socket is long enough to accept the 3 mm or 6 mm abutment 400 with either abutment screwed into the radicular portion of the TAD implant. The TAD implant 300 having the abutment 400 fitted thereon is then screwed into place through the surgical guide to one third or one half of the final depth. Next the operator takes a periapical x-ray to check the insertion path. If the path will avoid adjacent teeth or other anatomical areas such as cortical plates, etc. the operator may decide to replace the surgical guide and screw the TAD implant into its fully seated position. In this case the surgical guide was used for 100% of the osteotomy and insertion.

In still some embodiments, the operator could also make the decision to not use the surgical guide for the entire procedure. In that case the operator would turn or screw in the TAD implant 300 and attached abutment 400 (as a single unit) free hand (without the guide) to its fully seated position. Next the operator would have the patient gently and carefully close their teeth together to test the length of the 3 or 6 mm abutment 400 in relation to the opposing teeth. If the abutment (3 mm or 6 mm) 400 hits the opposite arch teeth, the abutment 400 is removed from the TAD implant platform 308 with an abutment hand tool, placed on the abutment holding tool and trimmed to size before reinserting the abutment 400 (of a reduced length of, for example, 2.5 mm).

Regardless of how the TAD implant becomes installed, following installation, In some embodiments, a second abutment 500 is fitted over the titanium abutment 400, and the length of the second abutment 500 is reduced as necessary. The second abutment may be used at the time of surgery (if there is sufficient initial stability of the TAD implant 300), or at approximately, 6 weeks to 2 months after surgery (to allow for preliminary osseointegration of the TAD implant sufficient for loading the TAD implant). In either instance, the first abutment 300 is temporarily removed, and the second abutment 500 is inserted (e.g, by operator's fingers) onto the TAD implant platform 308. The first abutment 400 is then screwed back down into the internal core 306 which locks the second abutment 500 into place. Alternatively, or in addition, the abutment 500 may be cemented to the TAD implant 300 and/or abutment 400.

While the invention has been particularly shown and described in conjunction with exemplary embodiments, it will be appreciated that variations and modifications will occur to those skilled in the art. For example, although the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with the present invention. Furthermore, the methods according to the present invention may be implemented in association with the formation and/or processing of structures illustrated and described herein as well as in association with other structures not illustrated. Therefore, it is to be understood that the appended claims are intended to cover all such modifications and changes that fall within the true spirit of the invention.

I claim:

1. A system comprising:
   a temporary anchorage device (TAD) implant, the TAD implant comprising:
      an implant portion;
      a platform disposed on one end of the implant portion; and
      a hexagonally-shaped head disposed on the platform, the hexagonally-shaped head having an interior comprising a cupped inner portion and a threaded core depending from the cupped inner portion, the threaded core having female threads for accepting a threaded portion of a first abutment the system further comprising a second abutment, the second abutment comprising: a graduated portion having a first end and a second end, a bulbous base disposed at the first end of the graduated portion of the second abutment, an inner canal expanding through the graduated portion of the second abutment and the bulbous base, the inner canal having a female hex, a first elevation extending partially around a circumference of an outer wall of the second abutment, a second elevation extending from a widest circumference of the bulbous base to the second end of the graduated portion; wherein the second abutment is affixed to the TAD implant such that the bulbous base is disposed on the hexagonally-shaped head, and the threaded portion of the first abutment traverses an interior of the second abutment and is coupled to the threaded core of the hexagonally-shaped head.

2. The system of claim 1, further comprising a first abutment, the first abutment comprising:
a graduated portion, and
a threaded portion connected to the graduated portion of the first abutment at a junction.

3. The system of claim 1, wherein the implant portion comprises self-tapping threads thereon.

4. The system of claim 1, wherein the hexagonally-shaped head has a length of 2 millimeters.

5. The system of claim 1, wherein the implant portion is comprised of titanium.

6. The system of claim 1, wherein the implant portion is comprised of stainless steel.

7. The system of claim 1, wherein the platform has a length of 0.5 millimeters.

8. The system of claim 1, wherein the implant portion descends from the hexagonally-shaped head at a taper angle.

9. The system of claim 1, wherein the abutment is comprised of titanium without a treatment with a chemical or biological coating.

10. The system of claim 2, wherein the graduated portion comprises a plurality of grooves that span a circumference of an outer portion of an exterior surface of the graduated portion.

11. The system of claim 1, wherein the second abutment is comprised of a radiopaque plastic.

12. The system of claim 1, wherein the second abutment is comprised of polyetheretherketone.

13. The system of claim 1, wherein the second abutment has a length ranging from 3 millimeters to 6 millimeters.

14. The system of claim 1 wherein the second abutment comprises a plurality of grooves formed on the graduated portion of the second abutment.

15. The system of claim 1, wherein the second elevation has a width of 1 millimeter.

16. The system of claim 2, wherein the first abutment is comprised of stainless steel.

* * * * *